United States Patent [19]

Shoesmith

[11] Plant 4,456

[45] Aug. 28, 1979

[54] CHRYSANTHEMUM NAMED ALPINE

[75] Inventor: Leonard H. Shoesmith, Westfield-Woking, England

[73] Assignee: Pan-American Plant Company, West Chicago, Ill.

[21] Appl. No.: 955,148

[22] Filed: Oct. 26, 1978

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Chas. W. Rummler

[57] ABSTRACT

A new pot chrysanthemum cultivar distinguished by its large white blooms having light cream centers and its decorative flower form with firm ray florets which have good shelf life, and by its upright plant habit with durable foliage and strong stems providing a plant which performs well when flowered year around on tall treatment.

4 Drawing Figures

BACKGROUND OF THE NEW PLANT

This new cultivar of chrysanthemum originated as a seedling of unidentified parentage grown from seeds of random pollinated plants produced in greenhouse at Westfield-Woking, Surrey, England. This plant was discovered by me in October 1973 and because of its beauty was reproduced by cuttings for test purposes. Propagation through successive generations in greenhouse at Westfield-Woking, by means of vegetative cuttings, has shown this new plant to have important and commercially advantageous characteristics which hold true from generation to generation and which appear to be firmly fixed. This new plant is now being asexually propagated on a commercial scale at West Chicago, Ill., and at Cortez, Fla.

DESCRIPTION OF THE DRAWINGS

This new chrysanthemum cultivar is illustrated by the accompanying drawings, the first sheet of which shows the form and color of blooms by means of conventional photographic procedures and the second of which, by mechanical reproduction of photocopies, shows the form of typical leaves of the plant.

DESCRIPTION OF THE NEW PLANT

The following is a detailed description of this new chrysanthemum variety, as observed in April and May in greenhouse at West Chicago, Ill., with the color designations being according to The R.H.S. Colour Chart published by The Royal Horticultural Society of London, England.

THE PLANT

Origin: Seedling.

Parentage: Unknown, this seedling having been selected from plants resulting from random crosses.

Classification:

*Botanic.*—*Chrysanthemum morifolium.*

*Commercial.*—Greenhouse pot plant.

Form: Perennial herbaceous bush.

Height: 27 to 37 cm.

Growth: Upright, vigorous and terminal, with sturdiness and excellent strength.

Branching: Normal, under natural conditions.

Foliage: Quantity — Abundant with 6 to 8 leaves on about 10 cm. of stem.

*Leaf size.*—Length — about 5.8 to 11.8 cm. Width — about 3.9 to 7.0 cm.

*Leaf shape.*—Lobed and slightly serrated.

*Surface aspect.*—Canescent.

*Color.*—Upper side — 137A. Under side — 146A.

*Venation.*—Pinnate.

*Petioles.*—Length — about 1.1 to 2.5 cm.

THE BUD

Form: Elliptical.

Size:

*Diameter.*—About 9 to 11 mm.

*Depth.*—About 6 to 7 mm.

Opening rate: Slow.

Color:

*When phyllaries divide.*—144A.

*When florets begin to unfurl.*—2D.

Phyllaries: Many spear-shaped, upstanding involucral bracts on the outside of the receptacle.

*Color.*—Inside — 137C. Outside — 137C.

*Surface aspect.*—Pubescent.

Peduncle: Length — about 4 to 16 mm.

*Character.*—Sturdy and erect.

*Surface aspect.*—Pubescent.

THE FLOWER

Flowering character: Recommended year around with photoperiod control.

*Response.*—9 week.

*Natural season.*—October 23 to October 30.

Blooms:

*Flower type.*—Composite and decorative.

*Size.*—Large. Diameter: about 10.5 to 11.3 cm. Depth: about 4.5 to 6.5 cm.

*Shape.*—Cup-shaped when bloom first opens. Becomes generally hemispherical as bloom matures.

*Florets.*—Quantity — numerous.

*Form.*—Linear. Many with acute apex and some with obtuse apex.

*Color*—Outer florets: Upper side — 155A. Reverse side — 155A. Inside florets: Upper side — 4D. Reverse side — 4D.

*Firmness.*—Strong, resists deformation.

*Appearance.*—Very slight shine.

Discoloration, after full bloom: None.

Persistence: Florets hang on and dry.

Peduncle: Character — sturdy and upright.
*Length.*—About 4 to 16 mm.
*Color.*—137C.
Fragrance: Typical chrysanthemum.
Lasting quality: On plant — about 3 weeks. Not recommended for cut flower use.

REPRODUCTIVE ORGANS

Stamens: Number — 5.
*Arrangement.*—Syngenesious.
*Filaments.*—Length — about 2 to 4 mm.
*Color.*—Light yellow.
*Pollen.*—Color — yellow.
Pistils: Number — one for each ray and disc floret.
*Styles.*—Length — about 5 to 6 mm.
*Stigma.*—Color — yellow.
Ovaries: Inferior bicarpellate.

This cultivar of pot chrysanthemum is characterized by its white blooms with light cream centers and its decorative flower form, the size of its blooms which are about 10.5 to 11.3 cm. in diameter when grown as a disbud pot, and its firm ray florets which possess good shelf life. This variety is also characterized by its upright plant habit and its breaking ability, which averages 3 to 3½ breaks when manually pinched, its durable foliage and strong stems. This plant flowers 9 weeks after start of short-day treatment and performs well when flowered year around on tall treatment.

I claim:

1. A new and distinct cultivar of pot chrysanthemum, substantially as herein shown and described, characterized by its decorative flower form with large white blooms having light cream centers, by its upright plant habit, durable foliage and strong stems, its 9 week response, and its good performance when flowered year around on tall treatment.

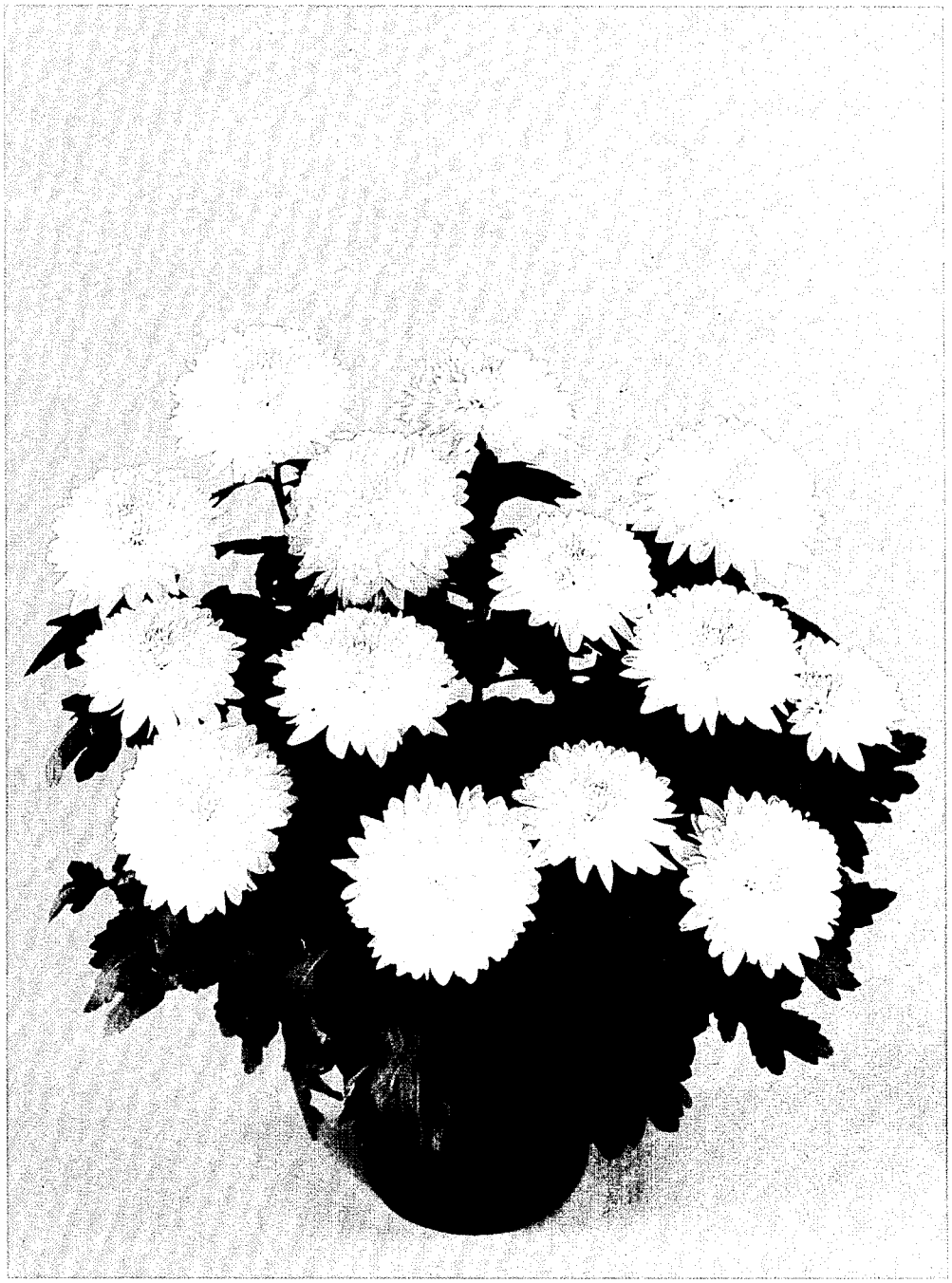

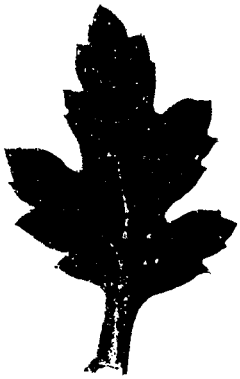
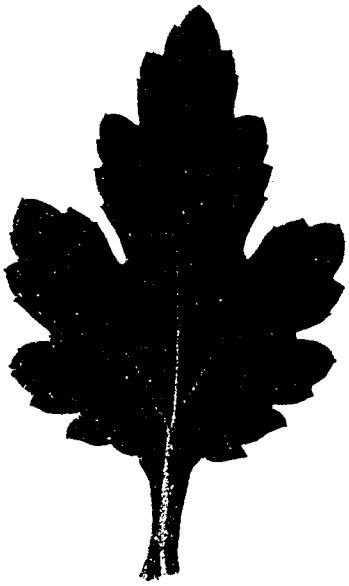
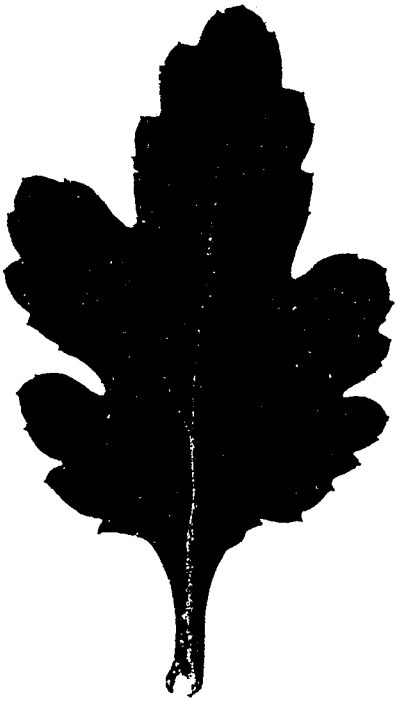

* * * * *